(12) United States Patent
Kniajanski et al.

(10) Patent No.: US 8,624,050 B2
(45) Date of Patent: Jan. 7, 2014

(54) SOLUTION PROCESS FOR TRANSPARENT CONDUCTIVE OXIDE COATINGS

(75) Inventors: Sergei Kniajanski, Clifton Park, NY (US); Aharon Yakimov, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 672 days.

(21) Appl. No.: 12/512,152

(22) Filed: Jul. 30, 2009

(65) Prior Publication Data
US 2009/0289235 A1 Nov. 26, 2009

Related U.S. Application Data

(63) Continuation-in-part of application No. 11/931,039, filed on Oct. 31, 2007, now Pat. No. 7,652,157.

(60) Provisional application No. 60/945,715, filed on Jun. 22, 2007.

(51) Int. Cl.
   *C07F 7/04* (2006.01)
   *C07F 7/08* (2006.01)

(52) U.S. Cl.
   USPC .......................................... 556/467; 556/10

(58) Field of Classification Search
   USPC .................................. 556/467, 10
   See application file for complete search history.

(56) References Cited

U.S. PATENT DOCUMENTS

| | | | |
|---|---|---|---|
| 4,525,565 A | 6/1985 | Laisney et al. | |
| 5,614,654 A | 3/1997 | Miyake et al. | |
| 7,416,688 B2 | 8/2008 | Pfaff et al. | |
| 7,476,603 B2 | 1/2009 | Grinwald et al. | |
| 7,507,618 B2 | 3/2009 | Dunbar | |
| 2004/0086643 A1 | 5/2004 | Onozawa et al. | |
| 2005/0112282 A1* | 5/2005 | Gordon et al. | 427/255.18 |
| 2006/0062902 A1 | 3/2006 | Sager et al. | |
| 2006/0110936 A1* | 5/2006 | Hill et al. | 438/778 |
| 2008/0031943 A1 | 2/2008 | Gupta et al. | |
| 2008/0138539 A1* | 6/2008 | Breitung et al. | 428/1.1 |
| 2008/0217576 A1 | 9/2008 | Stockum et al. | |
| 2009/0081826 A1 | 3/2009 | Cowdery-Corvan et al. | |

FOREIGN PATENT DOCUMENTS

| | | |
|---|---|---|
| EP | 1621258 A1 | 2/2006 |
| GB | 2428689 A | 7/2007 |
| JP | 09048787 A | 2/1997 |
| JP | 2003162923 A | 6/2003 |
| JP | 2003165841 A | 6/2003 |
| RU | 2064956 C1 | 8/1996 |
| WO | WO 0227063 A2 * | 4/2002 |

OTHER PUBLICATIONS

Wrobel, O. et al. "Siloxyaluminum alkyl cations: Synthesis, structures, and reactions related to activation of zirconocene catalysts on silica gel surfaces," Organometallics, (2003) 22: 1320-1325.*
Driess, M. et al. "Synthesis and structure of siloxy-substituted ZnO aggregates having (ZnO)n (n=2,4) and Zn3O4 cores," Eur. J. Inorg. Chem. (2000) 2517-2522.*
Amo, V. et al. "Neutral and cationic aluminum and titanium complexes incorporating sterically demanding organosilicon ligands," Organometallics (2005) 24: 2331-2338.*
Jana, S. et al. "Organozinc siloxide-hydrazide aggregates [(RZn)4(NHNMe2)x(OSiMe3)4-x]," Z. Naturforsch. (2006) 61B: 838-845.*
Barton, T., et al. "Organosilicon Chemistry. A brief overview" in Silicon-based Polymer Science, Zeigler, J. et al.,ed., Advances in Chemistry (ACS, Washington, D.C., 1989).*
Szyszka, "Transparent and Conductive Aluminum Doped Zinc Oxide Films Prepared by Mid-Frequency Reactive Magnetron Sputtering", Thin Solid Films, vol. 351, pp. 164-169, 1999.
Andrianov et al, "Titanodimethylsiloxane Oligomers", Inst. Heteroorg. Compounds, Moscow, Russia, Journal Written in Russian, Abstract Only, 1 page, 2006.
Alaeddine et al., "Influence of Al Dopant on the Optical and Electrical Properties of Zinc Oxide Thin Films Prepared by Spray Pyrolysis", Journal of Applied Sciences, vol. 9, Issue 8, pp. 1588-1592, 2009.
Ellmer et al., "2.3 Outlook: Higher Electron Mobilities in Zinc Oxide", Transparent Conductive Zinc Oxide, Basics and Applications in Thin Film Solar Cells, pp. 67-70, Aug. 2007.
Co-pending, U.S. Appl. No. 11/931,039, filed Oct. 31, 2009 entitled "Metal Oxide Coatings".
Co-pending, U.S. Appl. No. 11/930,991, filed Oct. 31, 2009 entitled "Metal Oxide Coatings".
Unofficial English translation of Chinese Office Action dated Mar. 1, 2012 from corresponding CN Application No. 200810191117.7.

* cited by examiner

*Primary Examiner* — Johann R Richter
*Assistant Examiner* — Amy C Bonaparte
(74) *Attorney, Agent, or Firm* — Mary Louise Stanford

(57) ABSTRACT

A process according to the present invention comprises combining in a reaction mixture at least one metal alkyl compound of formula $MR_x$ with at least one silanol compound of formula;

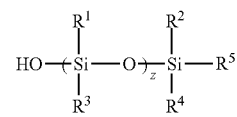

forming a film from the reaction mixture; and
treating the film with heat and moisture;
wherein an amount of the at least one silanol compound present ranges from about one quarter to about three quarters of an amount required to replace all alkyl groups of the at least one metal alkyl compounds with groups derived from the at least one silanol compound;
M is, independently at each occurrence, Zn, Cd, Al, Ga, In, Tl, Hg, Pb, Bi or a combination thereof;
x is, independently at each occurrence, an integer equal to 2 or 3;
z is 0, 1 or 2;
R is, independently at each occurrence, alkyl; and
$R^1$-$R^5$ is independently H, alkyl, or hydroxyl.

12 Claims, No Drawings

US 8,624,050 B2

SOLUTION PROCESS FOR TRANSPARENT CONDUCTIVE OXIDE COATINGS

CROSS REFERENCE TO RELATED APPLICATIONS

This application is a continuation-in-part of U.S. application Ser. No. 11/931,039, filed on 31 Oct. 2007, which is a non-provisional of and claims priority from U.S. Provisional Patent Application Ser. No. 60/945,715, filed on Jun. 22, 2007; the entire contents of both of which is incorporated herein by reference.

BACKGROUND

New and emerging PV devices are often based on the use of lower-cost semiconductors, thin films of conventional semiconductors, and organic-inorganic hybrids. Many of these PV devices are rapidly attaining commercial viability. In some cases, thin film layers are deposited by solution processible methods, which are attractive from a cost and manufacturability perspective. However, all such approaches currently use transparent conducting windows (transparent conductive oxides, TCO) deposited by conventional vacuum-based methods, which sacrifices much of the potential cost and scalability advantages.

Transparent conducting oxides are critical components of both existing and emerging approaches to high-efficiency, low-cost PV devices. TCOs act as electrode elements and diffusion barriers, and their work function influences the open-circuit voltage, thus affecting device efficiency. The basic characteristics of TCO materials include high optical transmissivity across a wide spectrum range and high conductivity. TCO for terrestrial PV applications must also be cost effective. The variety of emerging PV cell types dictates the broad range of TCO material requirements. In many cases, current TCO materials do not satisfy the needs of emerging PV technologies. To maximize the potential of PV devices, it is therefore increasingly important to develop new and improved transparent conductors that are capable of supporting novel PV devices and process-specific requirements. In addition, these materials must have reduced sensitivity to material shortages and have improved scalability.

Three oxides are of major commercial importance today: indium oxide, tin oxide, and zinc oxide. Since the 1960s, tin-doped indium oxide (ITO) has been the most widely used TCO for optoelectronic device applications. Currently, this material offers the best available performance in terms of conductivity and transmissivity. In addition, this material offers excellent environmental stability, reproducibility, and good surface morphology. Not surprisingly, the indium oxide based family of materials currently is the most studied and best-understood TCO. The deposition of ITO in a manufacturing environment is typically done by magnetron sputtering. For high volume use, the cost of sputter targets figures strongly into the cost of the final product. Given the semiprecious nature of indium metal and its price instability (indium metal prices spiked at $900/kg in 2005), there are both economic and technical forces driving the development of alternative TCO materials. While new supplies of indium are available, they cannot be accessed cost-effectively by the mining industry without comprehensive market-driven planning. This means potential price volatility, as has been seen in the past, as sharp moves in demand create short-term price escalations. These factors make it unlikely that ITO can become a commodity product that device manufacturers require. Developing alternative TCO coatings that are composed of less-costly raw materials will eliminate this problem. Tin oxide based TCOs are the most deposited (by volume) today and are used mainly in architectural applications for energy-efficient windows. These windows are deposited by spray pyrolysis. Recent improvements in doped ZnO performance make this material an attractive replacement for ITO in future PV devices. Unfortunately, each major material group has drawbacks. As was mentioned, using indium-based materials as TCO for future PV devices is impeded by economical constraints, such as high indium price and significant price volatility. Zinc-based oxides require doping with Al or Ga. Ga is high price material (~$500 per kg), and doping with Al requires high degree of control in the $O_2$ sputtering atmosphere, thus challenging the robustness of the chemical composition uniformity across the film. In addition, the demonstrated conductivity of the zinc oxide or tin oxide based materials is inferior to ITO.

TCO films today may be prepared by a number of methods including sputtering, electron beam evaporation, chemical vapor deposition (CVD), pulsed laser deposition, spray pyrolysis, chemical bath and others. Magnetron sputtering is widely used for commercial production of different TCOs. However, this method requires relatively expensive high-vacuum equipment, is energy consuming, and imposes certain limitations on deposition substrate size and throughput. Worth noting, recent engineering advances and market drivers have significantly driven down the cost of sputtering equipment and improved manufacturability. For example, machines, which are capable of coating 1 m×3 m glass sheets from both sides or 60 cm×1 km plastic roll, are offered for 3 million euros. It is widely recognized that sputtering provides the best results in terms of high optical transparency and electrical conductivity of metal-oxide films, particularly ITO, ZnO, and ZnO—$Al_2O_3$. Nevertheless, sputtering has a limited ability to control the coating uniformity over large area (as the sputtering targets wear out) and limited capability to control composition of multi-component systems. Hence, compositions should be restrained to 2 components at best. The evaporation method (either thermal or e-beam) has similar drawbacks. The main drawback of producing TCO by metal-organic CVD is the limited availability of volatile precursors with relatively low decomposition temperature. For this reason, vacuum and/or high temperature (400-450° C.) equipment is often needed, which is incompatible with many PV devices. For similar reasons, spray pyrolysis, which is the most used process for tin oxide deposition, cannot be used for direct deposition of TCOs on top of PV structures.

A solution-based process would be economically attractive for TCOs. Recent developments suggested that TCO films can be prepared using solution-based processes such as sol-gel, metal-organic, and nano-powder inks or pastes. However, an economically viable solution-based process, which offers high performance TCO's has not yet been developed. The sol-gel process is inherently slow, requires slow drying and re-heating steps, and high temperature sintering. Therefore, sol-gel processes are incompatible with high-throughput, low-cost processes. For this reason, the sol-gel is often used for the preparation of nano-inks rather than for direct depositions. The metal-organic approach relies on high temperature (450-500° C.) decomposition. Inks and pastes based on nano-powder also require high temperature sintering because of the high degree of porosity of such films. Additionally, the conductivity of solution processed TCO films is usually 1-2 orders of magnitude inferior to that of prepared by sputtering. Thus, although solution-based approaches offer the possibility for large area production, applying these existing methods for PV is often precluded.

An alternative approach to form a transparent conductor for PV application is based on carbon nano-tube (CNT) inks. Currently demonstrated performance (conductivity and transparency) is inferior to traditional ITO or even ZnO. Certain process and material-related issues exist, such as the tendency to aggregate over time in solution. These issues result in high haze films and fixed work function, hence limiting PV applicability. While the attention given to this approach in the scientific community is indicative of an unfulfilled need for a viable solution to the transparent conductor problem, the method itself has not yet provided acceptable performance.

The number of compositions currently used as TCOs is restricted to a few primary and binary systems. This limitation is mainly due to two factors: 1) limited bulk solubility of crystalline metal oxide phases in each other, and 2) technical limitations of currently used processing methods. If these challenges could be overcome, it has been shown that the number of suitable transparent and conductive binary, ternary, and even quaternary phases may be larger. Some may potentially exist in thin films only since the phase separation in this case is kinetically precluded by the film thinness. Low-pressure or high-pressure CVD using solid volatile organometallic precursors is a convenient way to make a large variety of multicomponent TCOs. However, CVD requires high substrate temperature (400-450° C.) for precursor decomposition. Despite the fact that this method can be applied for large area production, it is limited to thermally stable substrates (like glass and metal foils) and cannot be applied for direct TCO layer deposition onto such PV structures as copper indium gallium diselenide (CIGS), CdTe, and organic PVs.

Plasma deposition has been reported as convenient way for continuous TCO deposition of certain zinc oxide based TCO's at mild temperature (200-250° C.). The method is based on burning metalalkyl derivatives in oxygen plasma directed to substrate, so metal oxide fragments reach and are deposited on the substrate. Despite its obvious advantages the applicability of this approach to real PV structures has not been yet demonstrated.

For PV applications, parts of the TCO coating must be removed to form a required pattern (e.g., to form monolithically-integrated series-interconnected devices). This is normally accomplished by photolithography or laser ablation. Among the most widely used TCO materials, zinc oxide is one of the easiest materials to etch, tin oxide is the most difficult to etch, and indium oxide is intermediate in etching difficulty. Photolithography is a slow multi-step process, and laser ablation is not suitable for high throughput, large area manufacturing.

Solution-based preparation of different parts of PV devices (amorphous silicon layer, CIGS layer, organic PVs, CdS layer, TCO has recently been the subject of intensive research. Continuous wet manufacturing of TCO would complement roll-to-roll fabrication of PV devices. While noticeable progress has been achieved by both academia and industry in high-throughput fabrication of various PV components, suitable solution-based low-temperature TCO production remains a challenge and may be the ultimate barrier to fully solution-processed PVs. Solution processed TCO may additionally benefit solar cells based on CIGS, which surface is rough and full of crevices. Sputtering TCO on such a surface does not smoothen the surface, and does not close up the morphology defects. As a result, such structures are vulnerable to moisture penetration during the operation, which causes the cell degradation. A convenient wet process might be potentially useful for solving this problem.

Though ITO can be used for CIGS, aluminum doped zinc oxide (AZO) work function better fits the needs of the CIGS cell. AZO layer can be fabricated by deposition of metal acetate and/or alcoholate solution in toluene-isopropanol mixture followed by drying and decomposition to metal oxides at 450-500° C. Such a high process temperature is harmful for the CIGS layer. The process is done in air and thus does not provide required control of oxygen content. Necessary activation by additional heating in vacuum is sometimes also reported. Besides the above, other disadvantages of this approach are: poor surface wetting by metal derivatives employed, and film porosity caused by specifics of zinc oxide crystallization kinetics. As a result, multiple depositions are required to achieve acceptable performance.

US2008319143 and US20080319212 report an alternative approach consisting in application of metal siloxanolates of general formula $M(OSiMe_2OSiMe_3)_n$ ($M(DM)_n$). Due to the liquid nature of these compounds and their structural similarity to silicones, their application obviously solves the problem of substrate wetting. It has been shown that spin coating solutions of Ti, V, Al, and Sn derivatives on glass and metal substrates leaves continuous liquid films, which are then converted into smooth solid films upon heating in humid air. Low electrical conductivity and doping abilities along with high optical transparency have been demonstrated for titania-vanadia compositions.

SUMMARY

In one aspect, the present invention relates to processes comprising combining in a reaction mixture at least one metal alkyl compound of formula $MR_x$ with at least one silanol compound of formula;

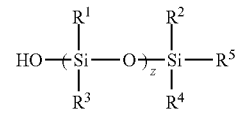

forming a film from the reaction mixture; and treating the film with heat and moisture;

wherein an amount of the at least one silanol compound present ranges from about one quarter to about three quarters of an amount required to replace all alkyl groups of the at least one metal alkyl compounds with groups derived from the at least one silanol compound;

M is, independently at each occurrence, Zn, Cd, Al, Ga, In, Tl, Hg, Pb, Bi or a combination thereof;

x is, independently at each occurrence, an integer equal to 2 or 3;

z is 0, 1 or 2;

R is, independently at each occurrence, alkyl; and $R^1$-$R^5$ is independently H, alkyl, or hydroxyl.

In another aspect, the present invention relates to transparent conductive oxide films prepared by a process of the present invention. In yet another aspect, the present invention relates to photovoltaic devices comprising a transparent conductive film prepared by a process of the present invention.

DETAILED DESCRIPTION

The present invention relates to processes comprising combining in a reaction mixture at least one metal alkyl compound of formula $MR_x$ with at least one silanol compound of formula;

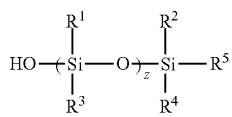

forming a film from the reaction mixture; and
treating the film with heat and moisture;
wherein an amount of the at least one silanol compound present ranges from about one quarter to about three quarters of an amount required to replace all alkyl groups of the at least one metal alkyl compounds with groups derived from the at least one silanol compound;
M is, independently at each occurrence, Zn, Cd, Al, Ga, In, Tl, Hg, Pb, Bi or a combination thereof;
x is, independently at each occurrence, an integer equal to 2 or 3;
z is 0, 1 or 2;
R is, independently at each occurrence, alkyl; and
$R^1$-$R^5$ is independently H, alkyl, or hydroxyl.

In particular embodiments, M is Zn, Al, In, or Ga, or M is Zn, Al, or In, or M is Zn or Al.

A single metal alkyl compound of formula $MR_x$ may be combined with the at least one silanol compound, or two or more may be combined to yield a mixed metal oxide coating. For example, an AZO coating may be prepared by combining a dialkyl zinc compound with a small amount of a trialkyl aluminum compound and a silanol compound. The metal alkyl compounds may be combined separately with the silanol and then all of the reactants combined together before forming a film.

In some cases, it may be desirable to use the lower alkyl analogues of the metal compounds, particularly the $C_{1-12}$ derivatives, more particularly the $C_{1-4}$ derivatives, or even the $C_{1-2}$ derivatives. For example, the reactions of $Zn(Et)_2$ and $AlMe_3$ (hexane solutions) with 2 or 3 equivalents of pentamethyldisiloxanol (MDOH) (solution in thf), respectively, rapidly go to $Zn(DM)_2$ and $Al(DM)_3$, and no resonances from metal-linked Et and Me groups are observed in proton spectra of the reaction products. Under some conditions, the reaction of $InBu_3$, however, stops at $InBu(DM)_2$, and triethyl- and trimethylindium may be more prone to complete conversion into $In(DM)_3$.

The amount of the at least one silanol compound present ranges from about one quarter to about three quarters of the amount required to replace all alkyl groups of the at least one metal alkyl compounds with groups derived from the at least one silanol compound, particularly from about one third to about two thirds of the amount required to replace all alkyl groups of the at least one metal alkyl compounds with groups derived from the at least one silanol compound. Higher amount of silanol compound may lead to the metal oxide film contamination with silicon containing products. Lower amount of silanol compounds results in pyrophoric precursors and low quality of metal oxide films.

The metal siloxanolate products of the reaction between the metal alkyl compounds and the silanols are typically liquids with excellent wetting properties on substrates of interest and/or soluble in common organic solvents and may be conveniently applied by common coating methods to form films. In addition, they are typically stable in dry air at room temperature, so they may be handled without any special precautions. When exposed to humid air at elevated temperatures, typically 50° C.-450° C., preferably 100° C.-200° C., the compounds are converted into metal oxides by hydrolysis with atmospheric moisture and/or thermal disproportionation. Byproducts are volatile low molecular weight siloxanes, which may be easily sequestered.

To form films, the metal siloxanolate compounds may be applied as neat liquids where applicable, in solvents or solvent mixtures that wet well the substrate of interest and are relatively volatile at process temperatures. In some cases, the liquid films may be handled under an inert atmosphere prior to hydrothermal treatment. The solvent may affect both hydrolysis kinetics and film properties. Polar and water miscible solvents may promote faster hydrolysis. Suitable solvents include alkanes such as hexanes, heptane, and octane; aromatics such as benzene, toluene, xylenes; dialkyl ethers such as dipropyl ether, diisopropyl ether, di-t-butyl ether, and dibutyl ether, monoglyme, and diglyme; cyclic ethers such as 1,4-dioxane, 1,3-dioxane, furan, tetrahydrofuran, pyran, tetrahydropyran, and the like, and mixtures thereof. Preferred solvents are hexanes, toluene, tetrahydrofuran, and dimethylformamide. A suitable amount of water, preferably purified water, may be added to the solution if desired in any manner, prior to, during, or subsequent to the preparation of the solution.

The films are treated with heat and moisture by heating at a temperature ranging from about 50° C. to about 450° C. in the presence of water vapor. Relative humidity typically ranges from about 5% to about 100%, preferably from about 25% to about 90%, and more preferably from about 40% to about 75%. Very little water is typically required, as other reactions that produce metal oxides and/or water may occur during the process. For example, dimerization of siloxanols released by the hydrolysis reaction may yield water, which can hydrolyze additional metal-ligand bonds. Metal-siloxane derivatives may also undergo thermal rearrangement without added water to produce M-O-M moieties. In some cases, it is desirable to perform the hydrothermal treatment of liquid films in an inert, or at least $CO_2$-free atmosphere to avoid formation of carbonates which decomposition requires temperatures >500° C. In addition, wet gas may be initially pumped at room temperature for a period of time necessary for the release and ventilation of the major part of MDOH formed in order to preclude formation of non-volatile siloxanes. Finally, it may be desirable to limit the temperature at which wet gas is pumped to less than about 330° C.

Acid catalysts may also increase the rate of the hydrolysis. Suitable acids include organic acids such as acetic acid, propionic acid and butyric acid. The amount of acid typically ranges from about 0.01 ppm to about 1000 ppm, based on total weight, preferably from about 0.1 ppm to about 10 ppm.

Substrates that may be coated in the processes of the present invention are only limited by their suitability for the end use, and may include glass, ceramics, plastics, metals, alloys, wood, paper, graphite, textiles, organic or inorganic substrates, such as various components of optical, electronic, or opto-electronic devices. Any method for producing a thin film on a substrate may be used, including conventional coating methods such as, but not limited to spin coating, dip coating, spray coating, and printing techniques, such as screen printing, ink-jet printing, gravure and rotogravure printing, flexography, offset printing, laser printing and pad printing. The coating or printing method and its parameters may affect properties of the film, such as thickness and uniformity, and may be adjusted to achieve a desired result. Parameters that may be adjusted may include, for example, type of solvent, precursor concentration, material amount, spin rate and spin time (for spin-coating), residence time (dipping and spray), and other relevant parameters, as will be apparent to the skilled in the art. Additionally, substrates may be wetted prior to the film deposition to improve the kinetics and uniformity of the hydrolysis process.

Where the substrate is heat-resistant, an additional annealing step may be performed. Annealing temperature ranges from about 200° C. to about 450° C.

The metal oxides that may be prepared by the processes of the present invention include monometallic oxides, polymetallic oxides, and doped oxide matrix systems, including, for example, $ZnO$, $In_2O_3$, $Al_2O_3$, $Ga_2O_3$, and binary, ternary, and quaternary oxides based thereon, such as $ZnO:(Al+Ga)$, $ZnO:(Al+In)$, $ZnO:(Al+Ga+In)$, $ZnO:(Al+Pb)$.

Preferred metal oxides are transparent conductive oxides (TCOs). In another embodiment, preferred metal oxides are semi-conducting oxides. In yet another embodiment, preferred metal oxides are catalytically active oxides. In another embodiment, preferred metal oxides are oxides that change their surface potential upon contact with common polluting gases including but not limited to carbon dioxide, carbon monoxide, nitrogen oxides, sulfur dioxide, ammonia, amines, aromatic hydrocarbons, etc. Metal oxides that include more than one metallic element may be prepared by combining more than one metal alkyl compounds with at least one silanol compound and subjecting the mixture to hydrothermal treatment. Depending on the process conditions, metal oxides may be prepared in monolythic, porous, meso-porous, or nano form. Metal oxides may be prepared as crystalline or amorphous phases.

The process of the present invention provides articles that include metal oxide coatings, particularly articles that include conductive or semiconductive metal oxide coatings, particularly thin film coatings which, depending on the nature of metal oxide, have high refractive index, high catalytic/photocatalytic activity, electrically conductive or semiconductive properties, non-linear optical properties, switching properties, barrier properties, and/or binding properties. The process may be used for production of transparent semiconductors and electrodes, sensors, high refractive index surfaces, such as windows, optics, ceramics, anti-reflective coatings, elements with catalytic properties for NOx reduction and/or removing sulfur from oil and fuels, protective coatings, anti-corrosion coatings, anti-static coatings, and barrier coatings for excluding organics, moisture, and/or gases. The process may also be used for fabricating transparent electrodes for photovoltaic devices, flat panel displays, touch panels, OLEDs, gradient refractive index layers in LED lamps and OLEDs, binding preformed metal oxide powders. Final properties of the coatings depend on the nature of the metal oxide.

In the context of the present invention, alkyl is intended to include linear, branched, or cyclic hydrocarbon structures and combinations thereof, including lower alkyl and higher alkyl. Preferred alkyl groups are those of $C_{20}$ or below. Lower alkyl refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7-20 carbon atoms, and includes n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl. Alkenyl and alkynyl refer to alkyl groups wherein two or more hydrogen atoms are replaced by a double or triple carbon-carbon bond, respectively.

Aryl and heteroaryl mean a 5- or 6-membered aromatic or heteroaromatic ring containing 0-3 heteroatoms selected from nitrogen, oxygen or sulfur; a bicyclic 9- or 10-membered aromatic or heteroaromatic ring system containing 0-3 heteroatoms selected from nitrogen, oxygen or sulfur; or a tricyclic 13- or 14-membered aromatic or heteroaromatic ring system containing 0-3 heteroatoms selected from nitrogen, oxygen or sulfur. The aromatic 6- to 14-membered carbocyclic rings include, for example, benzene, naphthalene, indane, tetralin, and fluorene; and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl and phenethyl. Heteroarylalkyl means an alkyl residue attached to a heteroaryl ring. Examples include pyridinylmethyl and pyrimidinylethyl. Alkylaryl means an aryl residue having one or more alkyl groups attached thereto. Examples are tolyl and mesityl.

Alkoxy or alkoxyl refers to groups of from 1 to 8 carbon atoms of a straight, branched, cyclic configuration and combinations thereof attached to the parent structure through an oxygen atom. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Heterocycle means a cycloalkyl or aryl residue in which one to two of the carbons is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted refers to residues, including, but not limited to, alkyl, alkylaryl, aryl, arylalkyl, and heteroaryl, wherein up to three H atoms of the residue are replaced with lower alkyl, substituted alkyl, aryl, substituted aryl, haloalkyl, alkoxy, carbonyl, carboxy, carboxalkoxy, carboxamido, acyloxy, amidino, nitro, halo, hydroxy, $OCH(COOH)_2$, cyano, primary amino, secondary amino, acylamino, alkylthio, sulfoxide, sulfone, phenyl, benzyl, phenoxy, benzyloxy, heteroaryl, or heteroaryloxy.

Haloalkyl refers to an alkyl residue, wherein one or more H atoms are replaced by halogen atoms; the term haloalkyl includes perhaloalkyl. Examples of haloalkyl groups that fall within the scope of the invention include $CH_2F$, $CHF_2$, and $CF_3$.

Siloxy refers to saturated linear, branched or cyclic structures and combinations thereof, based on a backbone having alternating silicon and oxygen atoms, each silicon atom separated from its nearest silicon neighbors by single oxygen atoms and substituted with 0-3 hydrogen, halo, alkyl or aryl groups.

EXAMPLES

Example 1

Preparation of Pentamethyldisiloxanol (Me$_3$SiOSiMe$_2$OH, MDOH)

20 ml of mentamethyldisiloxane (Gelest Inc., Tullytown Pa.) were slowly added to 30 ml of tetrahydrofuran containing 4 ml of water and 0.25 g of 10% Pd/C (Aldrich, Milwaukee Wis.) in ice bath under vigorous magnetic stirring. After gas release mainly ceased, the mixture was stirred for additional 4 hrs and was filtered. The filtrate was stirred with anhydrous MgSO$_4$ for 3 hrs and was filtered. The filtrate was stirred with powder CaH$_2$ for 1 hr, was then filtered, and the filtrate was re-condensed under vacuum from a flask at room temperature to a flask in liquid nitrogen. The silanol content was determined by $^1$H NMR analysis in methylene chloride. 45 wt % MDOH solution in dry tetrahydrofuran is stable for at least 30 days when stored at −40° C.

Example 2

Preparation of Zn—Al Precursors

Precursor solutions were prepared in a nitrogen glove box by mixing a measured amount of MDOH (45 wt % solution in thf) with a measured amount of a 1 M ZnEt$_2$-(5 at %) AlMe$_3$ mixture in hexanes (Aldrich) under vigorous magnetic stirring. After gas release has completed, solutions were filtered through a 0.45 micron PTFE filter. Solutions are stable at room temperature for 1-10 days. The solution stability decreases (a precipitate formation) with increased amount of MDOH added.

Example 3

Film Preparation, Hydrothermal Treatment and Film Analysis

Precursor solutions were span on glass slides in air for 1 min and then immediately placed into a quartz tube furnace purged with wet nitrogen. The furnace was purged with wet nitrogen for 15 min at room temperature, afterwards temperature was increased to 330° C., at which point wet nitrogen purge was changed for air purge. Temperature was increased to 450° C., air purge was changed for dry nitrogen flow for 15 min, afterwards the samples were quickly cooled to room temperature. The film thickness varied from 150 to 650 nm depending on the film deposition spin rate and precursor formulation. The film thickness increases with decreased amount of silanol. The films were analyzed by X-ray photo-electron spectroscopy (XPS), X-ray diffraction (XRD), scanning electron microscopy (SEM), and for their electrical properties.

Table 1 summarizes film analyses data for ZnO:5% Al. Elemental atomic percent were determined by XPS. Table 2 summarizes film electrical properties for films with variable Zn/Al ratio and MDOH/R ratio fixed at 2/3.

TABLE 1

| Film properties | MDOH/R | | | | | |
|---|---|---|---|---|---|---|
| | 1 | 3/4 | 2/3 | 1/2 | 2/5 | 1/3 |
| atomic % C | 1.5 | 0.7 | 0.4 | 2.6 | 1.4 | 0.0 |
| atomic % O | 58.1 | 55.3 | 55.7 | 54.4 | 52.5 | 51.9 |
| atomic % Zn | 25.9 | 41.4 | 41.6 | 40.2 | 43.8 | 46.0 |
| atomic % Al | 1.4 | 2.5 | 2.6 | 2.8 | 2.3 | 1.8 |
| atomic % Si | 13.1 | 0.6 | 0.2 | 0.3 | 0.0 | 0.0 |
| Phase | | crystal | crystal | crystal | amorph | amorph |
| Sheet resistance MΩ/ | >40 | 6 | 1 | 2 | 8 | >40 |
| Film morphology | dense | meso porous | porous | nano porous | porous | porous |

TABLE 2

| At. % Al | Sheet resistance, MOhm/sq |
|---|---|
| 1 | ~20 |
| 2 | ~6.0 |
| 5 | ~1.0 |
| 7.5 | ~0.2 |
| 10 | ~8.0 |
| 15 | >40 |

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A process comprising
combining in a reaction mixture at least one metal alkyl compound of formula MR$_x$ with at least one silanol compound of formula;

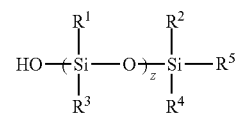

forming a film from the reaction mixture; and
treating the film with heat and moisture to form a metal oxide film comprising ≤0.6 atomic % silicon;
wherein an amount of the at least one silanol compound present ranges from about one quarter to about three quarters of an amount required to replace all alkyl groups of the at least one metal alkyl compounds with groups derived from the at least one silanol compound;
M is, independently at each occurrence, Zn, Cd, Al, Ga, In, Tl, Hg, Pb, Bi or a combination thereof;
x is, independently at each occurrence, an integer equal to 2 or 3;
z is 1 or 2;
R is, independently at each occurrence, alkyl; and
R$^1$-R$^5$ is independently H or alkyl.

2. A process according to claim 1, comprising combining at least two metal alkyl compounds of formula MR$_x$ with the at least one silanol compound.

3. A process according to claim 1, wherein the at least one metal alkyl compound of formula MR$_x$ is ZnR$_2$.

4. A process according to claim 1, comprising combining $ZnR_2$ and $AlR_3$ with the at least one silanol compound of formula I.

5. A process according to claim 1, wherein R is $C_{1-12}$ alkyl.

6. A process according to claim 1, wherein R is $C_{1-4}$ alkyl.

7. A process according to claim 1, wherein M is Zn, Al, In, Ga, or Cd.

8. A process according to claim 1, wherein M is Zn, Cd, Al, Ga, In, Pb, Bi or a combination thereof.

9. A process according to claim 1, wherein the amount of the at least one silanol compound present ranges from about one third to about two thirds of the amount required to replace all alkyl groups of the at least one metal alkyl compounds with groups derived from the at least one silanol compound.

10. A process according to claim 1, wherein the amount of the at least one silanol compound present ranges from about two fifths to about three fifths of the amount required to replace all alkyl groups of the at least one metal alkyl compounds with groups derived from the at least one silanol compound.

11. A process according to claim 1 wherein both the metal alkyl compound of formula $MR_x$ and the at least one silanol compound are dissolved in one or more solvents.

12. A process according to claim 1, wherein the amount of the at least one silanol compound present is about two thirds of the amount required to replace all alkyl groups of the at least one metal alkyl compounds with groups derived from the at least one silanol compound.

* * * * *